United States Patent
Wietfeld et al.

(10) Patent No.: US 7,449,587 B2
(45) Date of Patent: Nov. 11, 2008

(54) PROCESS FOR THE SYNTHESIS OF PEPTIDES CONTAINING A 4-HYDROXY-PROLINE SUBSTRUCTURE

(75) Inventors: Bernhard Wietfeld, Efringen-Kirchen (DE); Walter Prikoszovich, Schoenenbuch (CH); Bernhard Erb, Gipf-Oberfrick (CH); Werner Pachinger, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 11/839,565

(22) Filed: Aug. 16, 2007

(65) Prior Publication Data

US 2008/0021225 A1    Jan. 24, 2008

Related U.S. Application Data

(62) Division of application No. 10/538,028, filed as application No. PCT/EP03/14082 on Dec. 11, 2003, now Pat. No. 7,294,722.

(30) Foreign Application Priority Data

Dec. 12, 2002 (GB) ................... 0229020.3
Dec. 16, 2002 (GB) ................... 0229280.3

(51) Int. Cl.
*C07D 207/12* (2006.01)
(52) U.S. Cl. ...................................... 548/532
(58) Field of Classification Search ............... 548/532
See application file for complete search history.

(56) References Cited

FOREIGN PATENT DOCUMENTS

| DE | 43 06 839 | 9/1994 |
| WO | 97/01579 | 1/1997 |
| WO | 02/10192 | 2/2002 |

OTHER PUBLICATIONS

Bandaranayake et al., "Anomalous Acetoxylation of Aromatic Nuclei: Some Structural Requirements in the Substrate," Aust. J. Chem., vol. 34, No. 1, pp. 115-129 (1981).
Walter, "Beyer Walter—Lehrbuch Der Organischen Chemie," S. Hirzel Verlag, Stuttgart, Germany, p. 188, paragraph 2.20.2.2 (1988).
Hellwinkel et al., "Tieffarbige, durchkonjugierte Multi-Triphenylmethykium-Ionen," Angew. Chem., vol. 99(8), pp. 822-823 (1987).

*Primary Examiner*—Laura L. Stockton
(74) *Attorney, Agent, or Firm*—Gregory C. Houghton

(57) ABSTRACT

The present invention relates to processes for preparing peptides and to intermediates involved in such processes, e.g. a process for preparing a compound of formula VIII

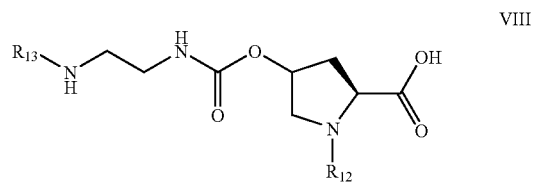

wherein $R_{12}$ and $R_{13}$ are as defined herein.

2 Claims, No Drawings

PROCESS FOR THE SYNTHESIS OF PEPTIDES CONTAINING A 4-HYDROXY-PROLINE SUBSTRUCTURE

This application is a divisional of U.S. application Ser. No. 10/538,028, filed Mar. 1, 2006, which is a 371 of International Application No. PCT/EP03/14082, filed Dec. 11, 2003.

The present invention relates to processes for preparing peptides and intermediates involved in such processes.

In one aspect, the invention relates to:

(A) a process for preparing a compound of formula I

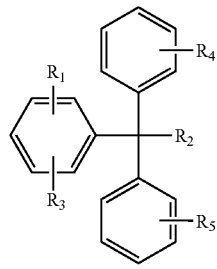

I wherein $R_1$ is a reactive substituent or an attachment to a solid phase;

$R_2$ is a reactive substituent; and $R_3$, $R_4$ and $R_5$ are each independently hydrogen or one or more substituents attached to each benzene ring and selected from hydroxy, amino, $C_{1-10}$-alkyl, $C_{1-10}$-alkoxy, $C_{1-10}$-alkylamino, di-$C_{1-10}$-alkylamino, carbamoyl, $C_{1-10}$-alkylcarbamoyl, di-$C_{1-10}$-alkylcarbamoyl, halo-$C_{1-10}$-alkyl, halogeno and nitro;

in free or salt form; comprising (a) reacting a compound of formula VI with an electrophile:

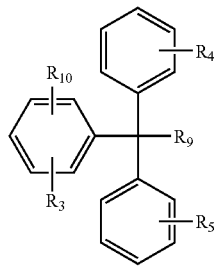

VI wherein $R_3$, $R_4$ and $R_5$ are as defined above;

$R_9$ is —OH, —OM or —OMX, where M is metal and X is a nucleophilic substituent;

$R_{10}$ is -M or -MX, where M is metal and X is a nucleophilic substituent;

in free or salt form;

and hydrolyzing the resulting compound to form a compound of formula I wherein $R_2$ is hydroxy;

(b) optionally converting a compound of formula I wherein $R_2$ is hydroxy to a compound of formula I wherein $R_2$ is other than hydroxy;

(c) optionally converting $R_1$ in a compound of formula I to an alternative $R_1$ group;

(d) optionally deprotecting a compound of formula I in protected form; and (e) where required, converting a compound of formula I obtained in free form into the desired salt form, or vice versa;

(B) a process for the preparation of a solid phase support system, comprising preparing a compound of formula I by a process as defined above, and coupling the compound with a suitably derivatised or functionalised solid phase material;

(C) a compound of formula V in free or salt form

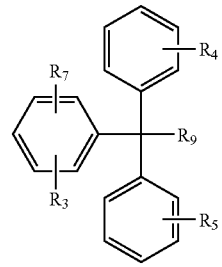

V wherein $R_3$, $R_4$, $R_5$, and $R_9$ are as defined above; and $R_7$ is a nucleophilic substituent;

(D) a compound of formula VI in free or salt form

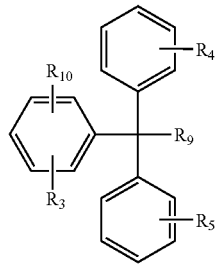

VI wherein $R_3$, $R_4$, $R_5$ and $R_9$ are as defined above; and $R_{10}$ is -M or -MX, where M is metal and X is a nucleophilic substituent.

The present invention provides a simple route for the preparation of compounds of formula I, which are useful for solid phase chemical synthesis. The process of the invention may directly produce a compound of formula I attached to a solid phase, or where $R_1$ is a reactive substituent, the compound of formula I can easily be coupled to a solid phase at a later stage. The presence of the reactive substituent $R_2$ permits the use of the compounds of formula I as linkers in the synthesis of oligomers and polymers, such as glycopeptides, nucleotides and proteins, especially in the solid phase synthesis of peptides. The compounds of formula I, particularly where $R_2$ is halogeno, may also be used as protecting agents for protecting functional groups, e.g. amino or hydroxy groups, in chemical synthesis.

The compounds of formula V and VI are useful as intermediate compounds in the preparation of compounds of formula I.

A compound of formula VI may be prepared by reacting a compound of formula V with a metal or organometallic compound:

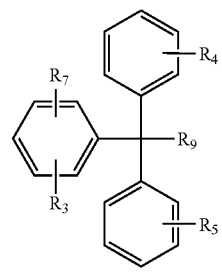

V wherein $R_3$, $R_4$, $R_5$ and $R_9$ are as defined above; and $R_7$ is a nucleophilic substituent.

A compound of formula V may be prepared by:

(i) reacting a compound of formula II with a metal or organometallic compound

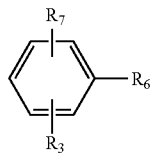

II wherein $R_6$ and $R_7$ are each a nucleophilic substituent and $R_3$ is as defined above and is protected if necessary by a removable protecting group; and (ii) reacting the compound obtained in (i) with a compound of formula III

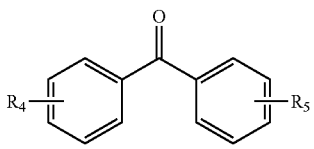

III wherein $R_4$ and $R_5$ are as defined above and are protected if necessary by a removable protecting group.

The process of the present invention may suitably be performed in a single reaction vessel without intermediary isolation.

Terms used in the specification have the following meanings:

"Alkyl" may be straight or branched. Preferably alkyl is $C_{1-4}$-alkyl.

"Alkoxy" may be straight or branched alkoxy. Preferably alkoxy is $C_{1-4}$-alkoxy.

"Acylamino" denotes a group of formula —NH—C(O)—R where R is straight chain or branched $C_{1-10}$-alkyl, cycloalkyl or aryl. Preferably R is $C_{1-4}$-alkyl.

"Acyloxy" denotes a group of formula —O—C(O)—R where R is as defined above.

"Aryl" is preferably $C_{6-10}$ aryl, e.g. phenyl.

"Halogeno" means fluoro, chloro, bromo or iodo.

"Haloalkyl" means straight chain or branched $C_{1-10}$-alkyl, substituted by one or more, for example one, two or three halogen atoms, preferably fluorine or chlorine atoms. Preferably haloalkyl is $C_{1-4}$-alkyl substituted by one, two or three fluorine or chlorine atoms.

"Organometallic compound" denotes a compound in which a carbon atom of an organic group is bound to a metal. The organometallic compound is preferably an alkylmetallic compound, for example an alkyllithium, e.g. a straight or branched chain $C_{1-10}$ alkyllithium compound or may alternatively be an arylmetallic compound, for example an aryllithium.

More preferably the alkyllithium compound is a $C_{3-6}$ alkyllithium compound, such as butyllithium or hexyllithium.

Alternatively, the organometallic compound may be an organomagnesium compound, for example a straight or branched chain alkylmagnesium or arylmagnesium compound, preferably a $C_{1-6}$ alkylmagnesium compound. Organomagnesium compounds are commonly known as Grignard reagents. The organomagnesium compound is preferably an organomagnesium halide, especially an iodide or bromide.

In further alternative embodiments, the organometallic compound may be an alkyl- or arylzinc compound, for example a $C_{1-6}$alkylzinc compound, or an $C_{1-6}$-alkyl- or aryltin compound.

M is preferably lithium or magnesium.

$R_1$ may be a reactive substituent suitable for linking the compound to a solid phase. $R_1$ may suitably be —C(O)R', —C(O)—OR', —C(O)—NR'R", —$R_{12}$—NR'R", —$R_{12}$—OR', —NR'R", or —C(O)X, wherein R' and R" are each independently hydrogen or straight or branched $C_{1-10}$-alkyl, e.g. $C_{1-4}$-alkyl, $R_{12}$ is straight or branched $C_{1-10}$-alkyl, e.g. $C_{1-4}$-alkyl, and X is a nucleophilic substituent, preferably halogeno, e.g. chloro. $R_1$ may suitably be in the para, ortho or meta position, preferably in the para position.

Alternatively $R_1$ may be an attachment to a solid phase material, e.g. polystyrene. Preferably the attachment is of the formula —C(O)—P, —C(O)—OP, —C(O)—NR'—P, —$R_{12}$—NR'—P, —$R_{12}$—OP, —NR'—P, —C(O)—$R_{12}$—P, —C(O)—O$R_{12}$—P, —C(O)—NR'—$R_{12}$—P, —$R_{12}$—NR'—$R_{12}$—P, $R_{12}$—O$R_{12}$—P, —NR'—$R_{12}$—P or —$R_{12}$—P, wherein R', R" and $R_{12}$ are as defined above and P is a solid phase material. More preferably $R_1$ is —C(O)—OP, —C(O)—O$R_{12}$—P, —C(O)—NH—P, —C(O)—NH—$R_{12}$—P, —NH—$R_{12}$—P or —$R_{12}$—P, wherein $R_{12}$ is methyl, e.g. —$CH_2$—P.

$R_2$ is preferably a reactive substituent suitable for linking the compound to a biological oligomer or polymer, or a monomer unit thereof, e.g. an amino acid or polypeptide. $R_2$ may suitably be hydroxy, acylamino, acyloxy, amino, halogeno, sulfhydryl, $C_{1-10}$-alkoxy or $C_{1-10}$-aryloxy, preferably halogeno.

Each benzene ring shown in formulae I to VII may be substituted by one or more groups. For example $R_3$ may designate one to four substituent groups, preferably one or two substituent groups, attached to the benzene ring shown in formulae I, II and IV to VII. $R_4$ and $R_5$ may designate one to five substituent groups, preferably one to three substituent groups, attached to each of the benzene rings shown in formulae I, II and IV to VII. Each substituent group may be present at any suitable position on the benzene rings to which they are attached. More preferably $R_4$ and/or $R_5$ is a substituent group at the ortho or para position on the benzene ring to which it is attached.

Each of $R_3$, $R_4$ and $R_5$ may be protected by a removable protecting group if necessary, e.g. when it contains an —OH or —$NH_2$ group which does not participate in the reaction. Protecting groups, their introduction and removal are described, for example, in "Protective Groups in Organic Synthesis", T. W. Greene et al., John Wiley & Sons Inc., Second Edition 1991. Preferably each of $R_3$, $R_4$ or $R_5$ is a group which does not require protection, e.g any of the groups listed above other than hydroxy, amino or nitro.

When $R_3$, $R_4$ or $R_5$ is halogeno, it Is preferably fluoro or chloro. When $R_3$, $R_4$ or $R_5$ is haloalkyl it is preferably trifluoromethyl. Preferably $R_3$ is $C_{1-4}$-alkyl, halogeno, or -hydrogen. Preferably $R_4$ and $R_5$ are each independently $C_{1-4}$-alkylcarbamoyl, di-$C_{1-4}$-alkylcarbamoyl, carbamoyl, trifluoromethyl, fluoro or chloro. Preferably $R_4$ and $R_5$ are the same. Preferably the nucleophilic substituents $R_6$ and $R_7$ are each independently halogeno, more preferably bromo or iodo, and most preferably $R_6$ and $R_7$ are each bromo. $R_7$ may suitably be in the para, ortho or meta position, preferably in the para position.

In one embodiment of the invention, the compound of formula II is first reacted with the metal or organometallic compound to form a compound of formula IV:

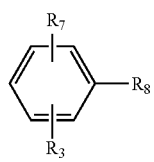

wherein $R_3$ and $R_7$ are as defined above and $R_8$ is -M or -MX, where M is metal and X is a nucleophilic substituent, preferably halogeno.

Where the metal is lithium or the organometallic compound is an organolithium compound, $R_8$ is —Li. Where the metal is magnesium or the organometallic compound is a Grignard reagent, $R_8$ is —MgX, and X is preferably halogeno. The compound of formula IV is then reacted with a compound of formula III to form a compound of formula V.

The compounds of formulae IV and V need not be separated or isolated but may be prepared in situ.

Suitable electrophiles for use in the process include carbon dioxide, isocyanates, nitriles, acyl halides (such as phosgene), leading to the formation of, for example, compounds of formula I wherein $R_1$ is carboxy, carbamoyl, alkylcarbamoyl or acyl. Alternatively the electrophile may be a derivatised solid phase material, e.g. a Merrifield polymer, enabling direct coupling of the compound of formula VI to a solid phase. In one embodiment the electrophile is a compound of formula X'—$(CH_2)_n$—P, wherein X' is a nucleophilic substituent e.g. halogeno or tosyloxy, n is an integer between 1 and 4, preferably 1, and P is a solid phase material.

Where the electrophile is carbon dioxide, the process preferably comprises first reacting the compound of formula V with a metal or organometallic compound to form a compound of formula VI as defined above and reacting, preferably in situ, the compound of formula VI with carbon dioxide.

Where the electrophile is carbon dioxide, preferably a compound of formula VII is formed:

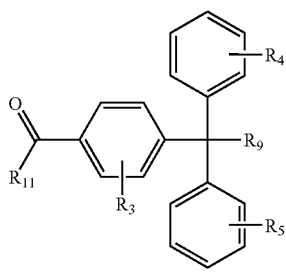

wherein $R_3$, $R_4$, $R_5$ and $R_9$ are as defined above; and $R_{11}$ is —H, —OM or —OMX, where M is metal and X is a nucleophilic substituent, preferably halogeno, in salt or free form.

Alternatively, the carboxylation step comprises reacting a compound of formula V with carbon dioxide in the presence of a metal or organometallic compound, to form a compound of formula VII.

The hydrolysis step preferably comprises reacting a compound of formula VII wherein $R_{11}$ is —OM or —OMX and/or $R_9$ is —OM or —OMX with water or an acid yielding a compound of formula I wherein $R_1$ is carboxy and $R_2$ is hydroxy, in salt or free form. Suitable acids include ammonium chloride, acetic acid, sulphuric acid and hydrochloric acid. A pH-buffered solution may also be used. Preferably a weak acid is used and/or the step may be carried out at a pH of 4 to 7. The reaction temperature may conveniently be −50 to 50° C., preferaby −10 to 10° C.

Alternatively the compound of formula VII where $R_{11}$ is —OM or —OMX may be reacted with a a nucleophile, e.g. an amine or halide, to form a compound of formula I wherein $R_1$ is —C(O)—NR'R" or —C(O)—X and R', R" and X are as defined above.

The process of the invention may conveniently be carried out in an inert organic solvent, preferably an ether solvent, for example diethyl ether, tetrahydrofuran or tert-butyl methyl ether. Alternatively a hydrocarbon solvent may be used. The reaction temperature for step (a) is conveniently −30 to +10° C., preferably −5 to −0° C. The reaction may, for example, be carried out using 0.5 to 2 equivalents, preferably 0.8 to 1.2 equivalents and most preferably about 1 equivalent of the metal or organometallic compound per equivalent of the compound of formula II. 0.5 to 2 equivalents, preferably 0.8 to 1.2 equivalents of the compound of formula III may be used per equivalent of the compound of formula II.

The temperature during the reaction of a compound of formula V with a metal or organometallic compound may conveniently be 0 to +50° C., preferably +20 to +30° C. The reaction temperature for the reaction with an electrophile (e.g. $CO_2$) may conveniently be 0 to −30° C., preferably −5 to −10° C. The hydrolysis step, e.g. with acid, may conveniently be performed at −10° C. to +10° C., e.g. 0 to +5° C. Preferably 0.5 to 2 equivalents, more preferably 0.8 to 1.2 equivalents of a metal or organometallic compound per equivalent of the compound of formula V are used.

The groups $R_1$ and $R_2$ may be converted to alternative $R_1$ and $R_2$ groups specified above by standard processes, such as by esterification, amidation or nucleophilic substitution. For example, a compound of formula I wherein $R_2$ is hydroxy may be converted to a compound of formula I wherein $R_2$ is halogeno by reaction with an acyl halide, e.g. acyl chloride.

Preferably the compound of formula I is in free form. The compounds in free or salt form can be obtained in the form of hydrates or solvates containing a solvent used for crystallization.

Compounds of formula I can be recovered from the reaction mixture and purified in a conventional manner.

The starting compounds of formula II or formula III are known or may be prepared by methods analogous to those known in the art. Organometallic compounds may be prepared by standard processes, for example by reaction of an alkyl or aryl halide with a metal, for example lithium or magnesium, suspended in diethyl ether or tetrahydrofuran. The organometallic compound is preferaby prepared and used in an inert (oxygen-free) anhydrous atmosphere, for instance under nitrogen.

The process according to the invention may suitably include a further step of coupling the compound of formula I wherein $R_1$ is a reactive substituent to a solid phase material. Suitable solid phase materials are disclosed, for example, in DE 4306839 A1, and include naturally occurring or synthetic organic or inorganic polymers in particulate form, e.g. as beads, or preferably as a surface layer on a suitable inert substrate material. Examples of suitable polymer materials include crosslinked polystyrene, e.g. polystyrene pins, Gly-HMD-MA/DMA pins and HEMA pins. The compound of formula I may conveniently be coupled to a solid phase material by reacting a group present on the solid phase with $R_1$. Thus the solid phase material preferably comprises reactive groups, such as amino groups. Preferably a compound of formula I, wherein $R_1$ is a carboxy group or an activated carboxy group, e.g. by reaction with diisopropylcarbodiimide, is reacted with a polymer bearing free amino groups.

A compound of formula I may be used as a linker. Thus the process according to the invention may also suitably include a further step of coupling the compound of formula I, optionally bound to a solid phase material, to a biological oligomer or polymer, or a monomer unit thereof. The compound may conveniently be coupled to the biological molecule, e.g. an amino acid or polypeptide, by reacting a group present on the biological molecule with $R_2$. For example, where $R_2$ is hydroxy and the biological molecule is a polypeptide or amino acid, the terminal carboxylic acid group of the biological molecule can be esterified by the $R_2$ hydroxy group, optionally via initial reaction of the compound of formula I with an acyl halide leading to in situ substitution of hydroxy by halogeno.

In a further aspect, the present invention provides:

(E) a process for preparing a compound of formula VIII

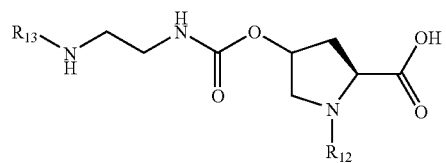

VIII wherein $R_{12}$ and $R_{13}$ are each a removable protecting group and $R_{12}$ and $R_{13}$ are different;

comprising reacting a compound of formula IX

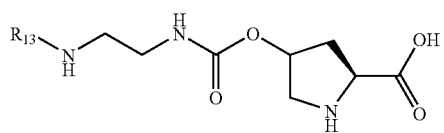

IX with a suitable $R_{12}$ donor compound;

(F) intermediates useful in the above process, defined by the general formula XIV

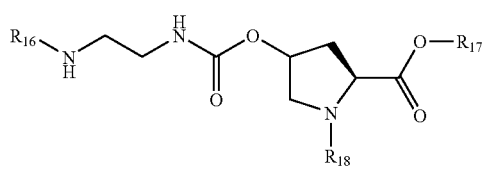

XIV wherein $R_{16}$ is a removable protecting group other than fluorenylmethoxycarbonyl, and is different to $R_{18}$;

$R_{17}$ is hydrogen or a blocking group removable by hydrolysis or hydrogenolysis; and $R_{18}$ is hydrogen or a removable protecting group other than fluorenylmethoxycarbonyl.

The present invention provides a simple and efficient route for the preparation of compounds of formula VIII, which are useful in the synthesis of peptides, for example as described in WO 02/10192. The compounds of formula XIV are useful as intermediate compounds in the preparation of compounds of formula VIII.

The compound of formula IX may be prepared from a compound of formula X

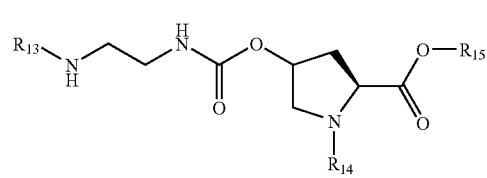

X wherein $R_{13}$ is as defined above, $R_{14}$ is a removable protecting group and $R_{14}$ is different to $R_{12}$ and $R_{13}$, and $R_{15}$ is a blocking group removable by hydrolysis or hydrogenolysis.

Protecting groups, their introduction and removal are described, for example, in "Protective Groups in Organic Synthesis", T. W. Greene et al., John Wiley & Sons Inc., Second Edition 1991. Suitable protecting group donor compounds, e.g. amino group protecting agents, are well-known to a skilled person, e.g. anhydrides, halides, carbamates or N-hydroxysuccinimides which provide one of the protecting groups below.

The protecting group $R_{12}$ is preferably fluorenylmethoxycarbonyl. $R_{13}$ or $R_{16}$ is preferably a protecting group other than fluorenylmethoxycarbonyl, and is preferably more resistant to removal by hydrolysis (for example base-catalysed hydrolysis) and/or hydrogenolysis than $R_{12}$ and/or $R_{14}$, e.g. more resistant than fluorenylmethoxycarbonyl and/or benzyloxycarbonyl. More preferably $R_{13}$ or $R_{16}$ is tert-butoxycarbonyl.

The protecting group $R_{14}$ or $R_{18}$ is preferably more resistant to removal by hydrolysis than $R_{12}$, e.g. more resistant than fluorenylmethoxycarbonyl. $R_{14}$ or $R_{18}$ is preferably removable by hydrogenolysis. Suitable $R_{14}$ or $R_{18}$ substituents include benzyloxycarbonyl, 1,1,-dimethylpropynyloxycarbonyl, vinyloxycarbonyl, N-hydroxypiperidinyloxycarbonyl, 9-anthrylmethyloxycarbonyl and phenylaminothiocarbonyl, allyl, nitrobenzyl, triphenylmethyl, (p-methoxyphenyl)diphenylmethyl, diphenyl-4-pyridylmethyl or benzylsulfonyl. Preferably $R_{14}$ or $R_{18}$ is an oxycarbonyl-containing protecting group, e.g. benzyloxycarbonyl(carbobenzoxy).

$R_{15}$ or $R_{17}$ may suitably be:

(i) $C_{1-10}$-alkyl, e.g. $C_{1-4}$-alkyl, preferably methyl, ethyl, propyl or butyl other than tert-butyl, more preferably methyl.

(ii) $C_{3-8}$-cycloalkyl, optionally substituted by one or more $C_{1-4}$ alkyl, e.g. methyl. Preferably cycloalkyl is $C_{3-6}$-cycloalkyl.

(iii) $C_{6-10}$-aryl, optionally substituted by one or more stabilising substitutents, e.g halogeno or nitro. Preferably aryl is phenyl, optionally substituted by one, two or three halogeno, e.g. chloro.

(iv) $(C_{6-10}$-aryl$)_{1-3}$-$C_{1-10}$-alkyl, optionally substituted on the aryl group by (i) one or more stabilising substituents, e.g halogeno or nitro, or (ii) by two substituents which together with the ring carbon atoms to which they are attached form a 5- or 6-membered ring, optionally containing one or two nitrogen or oxygen atoms. $(C_{6-10}$-aryl$)_{1-3}$-$C_{1-10}$-alkyl is preferably (i) (phenyl$)_{1-3}$-$C_{1-4}$-alkyl, more preferably benzyl, diphenylmethyl or triphenylmethyl, optionally substituted on each benzene ring by one, two or three halogeno, e.g chloro, (ii) anthrylmethyl, e.g. 9-anthrylmethyl, or (iii) piperonyl.

(v) $C_{6-10}$-aryl-$C_{1-4}$-alkoxy-$C_{1-4}$-alkyl, preferably benzyloxymethyl.

(vi) $C_{1-10}$-aryl-carbonyl-$C_{1-4}$-alkyl, preferably phenacyl.

Preferably $R_{15}$ or $R_{17}$ is a group which is removable by hydrogenolysis, such as benzyl, benzyloxymethyl, phenacyl, triphenylmethyl, piperonyl or 9-anthrylmethyl, preferably benzyl.

The compound of formula IX may be prepared by (i) hydrolysing the ester compound of formula X to obtain the corresponding carboxylic acid and (ii) removing the protecting group $R_{14}$. Preferably the hydrolysis step is performed before removal of the protecting group $R_{14}$. The protecting group $R_{14}$ may conveniently be removed by reductive hydrogenation (hydrogenolysis). This route, involving a hydrolysis step, is suitably followed when $R_{15}$ is not removable by hydrogenolysis. The hydrolysis step is preferably a base-catalysed hydrolysis, for example using sodium hydroxide and may suitably be performed in a polar solvent, e.g. methanol.

Alternatively, a compound of formula IX may conveniently be prepared by hydrogenation (hydrogenolysis) of a compound of formula X wherein $R_{15}$ is a group which is removable by hydrogenolysis, e.g. benzyl. The hydrogenation step may conveniently be performed using a suitable catalytic agent, for instance palladium-on-charcoal. Compound of formula X may be prepared by reacting a compound of formula XI

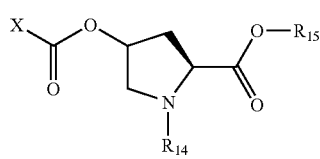

XI wherein X is a nucleophilic substituent and $R_{14}$ and $R_{15}$ are as defined above, with a compound of formula XII

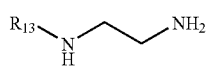

XII wherein $R_{13}$ is as defined above. This step may be performed in any suitable organic solvent, preferably in a hydrocarbon solvent, more preferably toluene.

The compound of formula XII is protected ethylenediamine, wherein one amino group has been protected with a removable protecting group. The nucleophilic substituent X in formula XI is preferably halogeno, such as fluoro, chloro, bromo or iodo, more preferably chloro. The compound of formula XI wherein X is halogeno may be formed by reaction of a compound of formula XIII

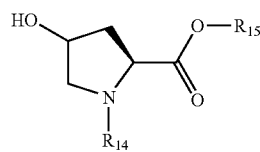

XIII with an acyl halide, for instance phosgene, tri-phosgene, phenylchloroformate or 4-nitrophenylchloroformate, preferably 4-nitrophenylchloroformate. This step may suitably be performed in the presence of an organic base, e.g. dimethylaminopyridine, in a non-polar solvent, e.g. toluene.

The compound of formula XIII may be commercially available, e.g. when $R_{15}$ is methyl or may be formed by esterification of 4-hydroxy-proline according to methods known in the art, for instance by reaction with benzyl alcohol or methanol. The resulting ester is then protected by reaction with a suitable $R_{14}$ donor compound, e.g. benzyloxycarbonyl-N-hydroxysuccinimide.

The compound of formula XI need not be separated or isolated, as the compound of formula XIII may be reacted with an acyl halide and the product of this reaction subsequently reacted with a compound of formula XII in the same vessel.

The addition of the protecting group $R_{12}$ to the compound of formula IX may suitably be performed in the presence of sodium carbonate/acetonitrile.

Compounds of formula VIII can be recovered from the reaction mixture and purified in a conventional manner.

In the compounds of formulae VIII-XI and XIII above, the oxy substituent on the proline may be in position cis or trans, preferably trans. The cis or trans isomers may be individually prepared, using the corresponding cis or trans hydroxyproline as starting material.

Insofar as the production of the starting materials is not particularly described, the compounds are known or may be prepared analogously to methods known in the art or as described thereafter.

In a further aspect, the present invention relates to a process for producing a compound of formula VIII, wherein $R_{12}$ is fluorenylmethoxycarbonyl and $R_{13}$ is a removable protecting group other than fluorenylmethoxycarbonyl, comprising reacting a compound of formula VIII with a fluorenylmethoxycarbonyl donor compound, e.g. fluorenylmethoxycarbonyl-N-hydroxysuccinimide.

The invention will now be described with reference to the following specific embodiments, in which the following abbreviations are used:

Fmoc=fluorenylmethoxycarbonyl
Boc=tert-butoxycarbonyl
Cbo=carbobenzoxy (benzyloxycarbonyl)
OSu=N-hydroxysuccinimide
HPTF=Heptane fraction
JT=Jacket temperature
HPLC=High performance liquid chromatography
THF=Tetrahydrofuran
TBME=Tert-butyl methyl ether
DMF=Dimethylformamide

EXAMPLE 1

Preparation of 4-(diphenyl-hydroxy-methyl)-benzoic acid 1,4-dibromobenzene (47.2 g, 0.2 M) is added to THF (240 ml). The clear solution is cooled to −65° C. A butyllithium solution (0.22 M, 94 ml of a 20% solution in CHX) is added over 30 minutes.

After 5 minutes of stirring a solution of benzophenone (36.4 g, 0.2 M in 180 ml THF) is added over 30 minutes (exothermic). The mixture is stirred for a further 30 minutes at −65° C. Then over 30 minutes the temperature is raised to −10° C. and the solution is stirred at this temperature for one hour.

The reaction mixture is then re-cooled to −65° C. Over 30 minutes a butyllithium solution (0.22 M, 94 ml of a 20% solution in cyclohexane) is added.

The resulting suspension is diluted with 200 ml THF. Then carbon dioxide gas is introduced over 90 minutes at −65° C. The temperature is raised to 20° C. and the mixture stirred overnight. The mixture is then cooled to 0° C. and an aqueous solution of ammonium chloride (120 ml of a 10% solution) is added over 30 minutes. 4-(diphenyl-hydroxy-methyl)-benzoic acid is formed at this stage.

The mixture is evaporated at 45° C. under a vacuum. The residue is adjusted to pH 4 with acetic acid and mixed with 400 ml $H_2O$. Extraction is performed with 2×150 ml ethyl acetate. The organic phases are extracted again with 100 ml water. The combined EST-phases are shaken with a 10% aqueous potassium hydroxide solution (2×120 ml). The combined aqueous phases are adjusted to pH 1-2 with hydrochloric acid at 20° C. and then extracted with 2×150 ml TBME. The combined TBME phases are mixed with 50 ml water and 50 ml saturated $Na_2SO_4$, dried with magnesium sulphate and evaporated at 45° C. under vacuum to obtain a crude product.

38.3 g crude product is dissolved in TBME (300 ml) at 40° C. The clear yellow solution is concentrated in a volume of 60 ml (240 ml TBME distilled off). The mixture is stirred for one hour at 40° C. (crystallisation). 50 ml HPTF is added, the mixture is cooled to 0° C. and stirred at 0° C. for 1 hour. Evaporating and washing with 2×15 ml heptane fraction and drying overnight at 45° C. under vacuum gives white crystals.

Attachment of 4-(diphenyl-hydroxy-methyl)-benzoic acid to a Solid Phase 15 g 4-(diphenyl-hydroxy-methyl)-benzoic acid with 7.54 g hydoxybenzotriazole is dissolved in 140 ml DMF by stirring for 15 min. 15.3 ml di-isopropylcarbo-di-imide is added and the solution kept at room temperature for 30 min. The solution is then stirred overnight at room temperature in the presence of aminomethylated polystyrene. After washing with DMF, methanol and THF the linker derivatised support is dried under vacuum.

EXAMPLE 2

Preparation of 4-(diphenyl-hydroxy-methyl)-benzoic acid (Alternative Method)

To 12 lt TBME in a well dried 100 lt Hastelloy-Reactor, 3.0 kg n-butyllithium (20% in cyclohexane; 9.37 mol) is added during a period of 20 min, keeping the temperature at −5° C. (clear solution). During a period of 30 min 2.00 kg 1,4-dibromobenzene (8.48 mol) dissolved in 16 l TBME is added keeping the temperature between −5° and 0° C. The addition container is rinsed with 3 l TBME.

After 30 min stirring at −5° C. a solution of 1.55 kg benzophenone (8.50 mol) in 8 lt TBME is added during a period of 20 min keeping the temperature between −5° and 0° C. The addition container is rinsed with 3 lt TBME. A very small amount of a white solid is formed. After 15 min stirring at −5° C. a process control sample (HPLC 1) is taken. The reaction mixture is stirred for further 25 min at −5° C. and warmed up to +25° C.

3.2 kg n-butyllithium (20% in cyclohexane; 10.00 mol) is added during a period of 25 min keeping the temperature between +25 and 27° C. The addition is slightly exothermic and the colour turned to slightly green. Some precipitate and froth are formed. After 20 min stirring a process control sample is taken (HPLC 2). Depending on the result of HPLC 2 further 0.3 kg n-buthyllithium is added after stirring at +25° C. for 35 min. After 15 min stirring a sample for process control is taken (HPLC 3). The lines of the n-buthyllithium addition are rinsed with 1.5 lt TBME and the reaction is cooled to −10° C.

1.99 kg dry ice (solid $CO_2$) is added portionwise during a period of 20 min keeping the temperature between −10 and −5° C. The reaction is exothermic and a slightly yellow precipitate is formed. After 15 min stirring at −10° C. 11 l TBME are added and the reaction mixture is warmed to 0° C. 5 l 18% aqueous hydrochloric acid is added during a period of 15 min keeping the temperature between 0° and +5° C. The addition is exothermic and the precipitate is dissolved (pH≦1).

The clear solution is transferred to a separation tank and the reactor is rinsed with 5 lt TBME. After separation of the aqueous phase the organic phase is washed with 20 lt water. After separation of the two layers the organic phase is extracted with 13 lt 5% aqueous KOH solution. The basic water phase is separated and the organic layer is extracted again with 13 lt 5% aqueous KOH solution. The combined basic aqueous layers are transferred to the 100 lt Hastelloy-Reactor. 22 l of TBME and 6 l aqueous 18% hydrochloric acid are added over a period of 20 min at a temperature between 0° and +5° C. The addition is exothermic and a white precipitate is formed but it dissolves again at a low pH-value (pH≦1 after HCl-addition). The mixture is stirred during 10 min and transferred to a separation tank. The layers are separated and the aqueous phase is extracted again with 16 l TBME. After separation of the layers the combined organic phases are concentrated at 500 mbar/45° C. JT to a volume of 4-5 l (32 l TBME are destilled off) and seed crystals are added. The temperature is raised up to 50° C. and 20 l HPTF are added slowly with good stirring. The white precipitate is stirred for 2 h at 50° C. JT. The jacked temperature is regulated at 0° C. and stirring is continued over night (16 h) letting cool down the suspension to 0° C. The white suspension is filtered off and the reactor is rinsed 5 times with 5 lt of the mother liquor. The residue is dried at 45° C. JT under vacuum (≧10 mbar) to constant weight (over night).

EXAMPLE 3

Preparation of Fmoc-(2S,4R)-Pro(4-OCO—NH—$CH_2$—$CH_2$—NH-Boc)-OH Starting from Cbo-(2S, 4R)-Pro(4-OH)—OMe 1. Dimethylaminopyridine (30.5 g, 250 mmol) and Cbo-(2S,4R)-Pro(4-OH)-OMe (34.9 g, 125 mmol) are dissolved in toluene (870 ml). A solution of 4-nitrophenylchloroformate (31.5 g, 157 mmol) in toluene (206 ml) is added dropwise to this solution at 0° C. to 5 ° C. over 20 minutes and stirred for an additional 2 hours. This is followed by addition of a solution of Boc-ethylenediamine (80.1 g, 500 mmol) in toluene (205 ml) and stirring at ambient temperature for 12 hours. A solution of concentrated sulfuric acid (43.7 g, 450 mmol) in water (873 ml) is then added while maintaining a temperature of 20° C. to 25° C. The white suspension is filtered by suction and washed with toluene (30 ml). The toluene phase is washed with water (450 ml), sodium carbonate (10% w/w, 450 ml) and three times with water (450 ml each). The toluene phase is azeotropically dried by distilling off 300 ml, which is continuously replaced by dry toluene (2×300 ml). Heptane (130 ml) is added to the dry toluene solution at 50° C. and cooled to 0° C. over two hours. The precipitated product is filtered, washed two times with toluene/heptane 1:2 v/v (70 ml), and dried at 50° C. under vacuum to leave Cbo(2S,4R)-Pro(4-OCO—NH—$CH_2$—$CH_2$—NH-Boc)-OMe as a white solid.

2. Cbo-(2S,4R)-Pro(4-OCO—NH—$CH_2$—$CH_2$—NH-Boc)-OMe (20.0 g, 43.0 mmol) is dissolved in a 1:1 mixture of tetrahydrofuran and methanol (380 ml). A 1 M sodium hydroxide solution (51.6 ml) is added and the resulting mixture stirred for 4 hours at ambient temperature. The mixture is adjusted to pH 3 by adding sulfuric acid (50 ml, 1 M). Tetrahydrofuran and methanol are distilled off at 50° C. and 50 mbar until no further solvents distil. The remaining milky solution is diluted with isopropyl acetate (113 ml) and water (57 ml), the phases are separated and the isopropyl acetate phase is washed with sodium chloride solution (10%, 113 ml). The solvent is distilled off (50 °C., 50 mbar) to yield a foam of Cbo-(2S,4R)-Pro(4-OCO—NH—CH$_2$—CH$_2$—NH-Boc)-OH (19.8 g), which was used without further purification in the next reaction.

3. Palladium on charcoal (10%, 1.94 g, 0042 mmol) is added to a solution of Cbo-(2S,4R)-Pro(4-OCO—NH—CH$_2$—CH$_2$—NH-Boc)-OH (19.4 g, 43.0 mmol) in isopropanol (350 ml) and water (37 ml). Hydrogen is bubbled through this mixture for 4 hours, the catalyst is filtered off, and the residue is washed with a mixture of isopropanol (50ml) and water (50 ml). The isopropanol/water phase is azeotropically dried by distilling off ⅔ of the volume, which is continuously replaced by a toluene/isopropanol mixture (1:1 v/v). The remaining dry solution is concentrated in vacuo to dryness (50 °C., 200 mbar) to leave (2S,4R)-Pro(4-OCO—NH—CH$_2$—CH$_2$—NH-Boc)-OH as a brownish solid, which was used without further purification.

4. (2S,4R)-Pro(4-OCO—NH—CH$_2$—CH$_2$—NH-Boc)-OH (5.0 g, 15 mmol) is dissolved in a mixture of water (25 ml) and triethylamine (1.5 g, 15 mmol) at 40 °C. A solution of Fmoc-OSu (4.65 g, 14 mmol) in acetonitrile (25 ml) is added to the clear solution over 30 minutes and stirred for 2 hours. Then the reaction mixture is adjusted to pH 3 with hydrochloric acid (1 m, 13 ml) and stirred for a further hour. Acetonitrile is distilled off (40° C., 80 mbar) and replaced by isopropyl acetate, affording a two-phase mixture. The lower aqueous phase is separated off, whilst the remaining organic layer is washed with water and distilled two times with replacement with isopropylacetate and then concentrated to a brownish foam. This foam is dissolved in isopropylacetate (25 ml) and added dropwise to heptane (200 ml) whereby the product is precipitated. The solid is filtered, washed with isopropylacetate/heptane and dried in vacuo at 40° C. to leave Fmoc-(2S,4R)-Pro(4-OCO—NH—CH$_2$—CH$_2$—NH-Boc)-OH.

EXAMPLE 4

Preparation of Fmoc-(2S,4R)-Pro(4-OCO—NH—CH$_2$—CH$_2$—NH-Boc)-OH starting from Cbo-(2S,4R)-Pro(4-OH)—OBzl The synthesis of Cbo-(2S,4R)-Pro(4-OH)—OBzl is described in T. Makoto, H. Guoxia, V. J. Hruby, J. Org. Chem. 2001, 66, 1038-1042. The process of example 3 is repeated, but using Cbo-(2S,4R)-Pro(4-OH)—OBzl in place of Cbo-(2S,4R)-Pro(4-OH)—OMe and performing steps 1, 3 and 4 only (omitting step 2).

EXAMPLE 5

Preparation of Fmoc-(2R,4R)-Pro(4-OCO—NH—CH$_2$—CH$_2$—NH-Boc)-OH

The process of example 3 or example 4 is repeated but using Cbo-(2R,4R)-Pro(4-OH)—OMe or Cbo-(2R,4R)-Pro(4-OH)—OBzl in place of Cbo-(2S,4R)-Pro(4-OH)—OMe or Cbo-(2S,4R)-Pro(4-OH)—OBzl.

EXAMPLE 6

Preparation of Fmoc-(2S,4S)-Pro(4-OCO—NH—CH$_2$—CH$_2$—NH-Boc)-OH

The process of example 3 or example 4 is repeated but using Cbo-(2S,4S)-Pro(4-OH)—OMe or Cbo-(2S,4S)-Pro(4-OH)—OBzl in place of Cbo-(2S,4R)-Pro(4-OH)—OMe or Cbo-(2S,4R)-Pro(4-OH)—OBzl.

The invention claimed is:

1. A compound of formula XIV

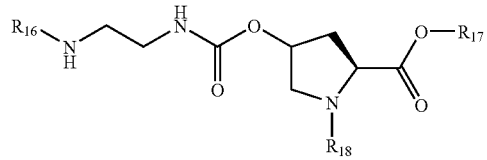

wherein $R_{16}$ is a removable protecting group other than fluorenylmethoxycarbonyl, and is different to $R_{18}$;

$R_{17}$ is hydrogen or a blocking group removable by hydrolysis or hydrogenolysis; and $R_{18}$ is hydrogen or a removable protecting group other than fluorenylmethoxycarbonyl.

2. A compound according to claim 1, wherein $R_{16}$ is tert-butoxycarbonyl.

* * * * *